United States Patent
Dollinger et al.

[11] Patent Number: 5,945,379
[45] Date of Patent: Aug. 31, 1999

[54] HERBICIDES BASED ON HETEROARYLOXY-ACETAMIDES FOR USE IN RICE CULTIVATION

[75] Inventors: Markus Dollinger, Leverkusen; Dieter Feucht, Monheim; Helmut Fürsch, Leichlingen, all of Germany

[73] Assignee: Bayer Aktiengesellschaft, Leverkusen, Germany

[21] Appl. No.: 08/856,827

[22] Filed: May 15, 1997

[30] Foreign Application Priority Data

May 24, 1996 [DE] Germany ............... 196 20 994

[51] Int. Cl.⁶ ............ A01N 25/32; A01N 43/824; A01N 43/54
[52] U.S. Cl. ............ 504/130; 504/106; 504/136; 504/143; 504/263
[58] Field of Search ............... 504/262, 263, 504/139, 130, 136, 143, 106

[56] References Cited

U.S. PATENT DOCUMENTS 4,968,342 11/1990 Förster et al. ............... 548/129

FOREIGN PATENT DOCUMENTS 0 348 737  1/1990  European Pat. Off. .

OTHER PUBLICATIONS

Ross et al., Soil Applied Herbicide Groups, "Applied Weed Science" (1985), Burgess Publishing Company, pp. 199–202.

*Primary Examiner*—S. Mark Clardy
*Attorney, Agent, or Firm*—Sprung Kramer Schaefer & Briscoe

[57] ABSTRACT

Heteroaryloxy-acetamides of the general formula (I)

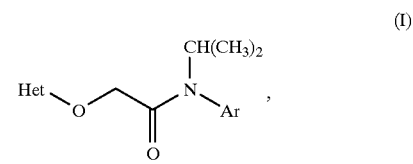

in which

Het represents thiadiazolyl which is substituted by halogen or by $C_1$–$C_4$-alkyl or phenyl, each of which is optionally substituted by halogen, and Ar represents optionally halogen-, $C_1$–$C_4$-alkyl- or $C_1$–$C_4$-halogenoalkyl-substituted phenyl.

can be used with good results as selective herbicides in rice cultivation.

The novel herbicidal active compound combinations comprising (1) a heteroaryloxy-acetamide of the formula (I) above and (2) in each case one active compound from the group of already known selective rice herbicides (e.g. bensulfuron, MCPB, and thiobencarb) exhibit, at certain weight ratios, synergistic activities and can be used particularly advantageously as selective herbicides in rice crops.

8 Claims, No Drawings

HERBICIDES BASED ON HETEROARYLOXY-ACETAMIDES FOR USE IN RICE CULTIVATION

The invention relates to novel herbicidal compositions and novel herbicidal synergistic active compound combinations containing known heteroaryloxy-acetamides and optionally other known herbicides belonging to other substance classes as active compounds which can be used particularly successfully for the selective control of weeds in rice cultivation.

Heteroaryloxy-acetamides are, as broadly active herbicides, the subject of a series of patent applications (cf. EP-A 5501, EP-A 18497, EP-A 29171, EP-A 94514, EP-A 100044, EP-A 100045, EP-A 161602, EP-A 195237, EP-A 348734, EP-A 348737, DE-A 4317323). However, the known heteroaryloxy-acetamides exhibit a number of gaps in their activity, in particular against dicotyledonous weeds.

Surprisingly it has now been found that a series of known herbicidally active compounds from the group of the heteroaryloxy-acetamides, as individual (reformulated) active compounds, exhibit, while being well tolerated by rice, very strong activity against weeds causing problems in this crop, or exhibit pronounced synergistic effects with respect to the activity against weeds when used together with active compounds from the group of compounds already known as herbicides for use in rice crops, and that they can be used particularly advantageously as broadly active products for the selective control of monocotyledonous as well as dicotyledonous weeds pre- and post- emergence in rice cultivation.

This invention accordingly provides (1) Herbicidal compositions for use in rice cultivation, characterized by an active content of at least one heteroaryloxy-acetamide of the general formula (I)

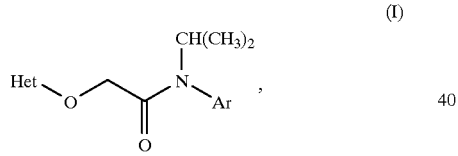

in which
Het represents thiadiazolyl which is substituted by halogen or by $C_1$–$C_4$-alkyl or phenyl, each of which is optionally substituted by halogen, and
Ar represents optionally halogen-, $C_1$–$C_4$-alkyl- or $C_1$–$C_4$-halogenoalkyl-substituted phenyl.

(2) synergistic herbicidal compositions for use in rice cultivation, characterized by an active content of an active compound combination comprising
(a) a heteroaryloxy-acetamide of the general formula (I)

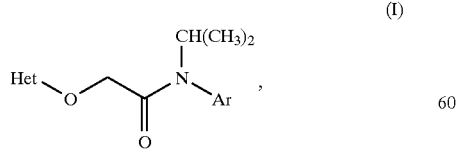

in which
Het represents thiadiazolyl which is substituted by halogen or by $C_1$–$C_4$-alkyl or phenyl, each of which is optionally substituted by halogen, and
Ar represents optionally halogen-, $C_1$–$C_4$-alkyl- or $C_1$–$C_4$-halogenoalkyl-substituted phenyl,
(active compound of group 1), and
(b) one or more compounds from the following group of herbicidally active compounds for use in rice crops ("rice herbicides", named by common names or code numbers):
AKD-741, amiprophos(-methyl), anilofos, benfuresate, bensulfuron(-methyl), bensulide, bentazone, benthiocarb (thiobencarb), benzofenap, bifenox, bromobutide, bromoxynil, butachlor, butamifos, butenachlor, cafenstrole (CH-900), chlomethoxyfen (X-52), chlormethoxynil, chlornitrofen, cinmethylin, CL-303569, CL-303578, cinosulfuron, clomeprop, cumyluron, cyclosulfamuron (AC-322140), cyhalofop(-butyl) (DEH-112), 2,4-D, dichlorprop, dimepiperate, dimethametryn, dithiopyr, DPX-47, diuron, dymron (daimuron, dimuron), esprocarb, etobenzanid, fenoxaprop A, fenoxaprop-P-ethyl, fluazifop-butyl, flurenol-n-butyl, GS-32911, haloxyfop, haloxyfop M, hexazinone, HOE-404, HOE-30374, HOK-7501 (HOK-1566), HW-52, imazosulfuron, JC-940, KUH-911 (KIH-2023), KUH-920, KNW-242, KPP-314, MCPA, MCPB, mefenacet, metsulfuron M, molinate, NC-310, NC-311, naproanilide, nitrofen, NSK-850, oxadiargyl (RP-020630, MY-100), oxadiazon, oxyfluorfen, piperophos, pretilachlor, prometryne, propanil, pyrazolate, pyrazosulfuron (-ethyl), pyrazoxyfen, pyributicarb, quinclorac, quizalofop A, sethoxydim, simetryne and trifluralin,
(active compounds of group 2),
generally in each case from 0.001 to 1000 parts by weight of one or more of the "rice herbicides" mentioned (from group 2) being present per part by weight of active compound of the formula (I) (from group 1);

(3) Method for the selective control of weeds in rice crops, characterized in that heteroaryloxy-acetamides of the above formula (I) according to point (1) and/or active compound combinations according to point (2) are allowed to act on the rice paddies;

(4) Use of heteroaryloxy-acetamides of the formula (I) according to point (1) and/or of active compound combinations according to point (2) for the selective control of weeds in rice crops;

(5) Process for the preparation of herbicidal compositions according to point (1) or of synergistic herbicidal compositions according to point (2), characterized in that heteroaryloxy-acetamides of the above formula (I) or active compound combinations according to (2) are mixed with extenders and/or surface-active agents.

Of particular interest are herbicidal compositions according to the invention which are characterized by an active content of a heteroaryloxy-acetamide of the formula (I) in which
Het represents 1,2,4-thiadazolyl or 1,3,4-thiadiazolyl, each of which is substituted by fluorine, chlorine, bromine or respectively optionally fluorine- and/or chlorine-substituted methyl, ethyl, n- or i-propyl or phenyl, and
Ar represents optionally fluorine-, chlorine-, bromine-, methyl- or trifluoromethyl-substituted phenyl.

Of particular interest are furthermore synergistic herbicidal compositions according to the invention which are characterized by an active content of an active compound combination comprising (a) a heteroaryloxy-acetamide of the formula (I) in which
Het represents 1,2,4-thiadiazolyl or 1,3,4-thiadiazolyl, each of which is substituted by fluorine, chlorine, bromine or respectively optionally fluorine- and/or chlorine-substituted methyl, ethyl, n- or i-propyl or phenyl, and
Ar represents optionally fluorine-, chlorine-, bromine-, methyl- or trifluoromethyl-substituted phenyl (active compound of group), and (b) one or two compounds from the following group of herbicidally active compounds for use in rice crops ("rice herbicides", named by common names or code numbers):
AKD-741, amiprophos(-methyl), anilofos, benfuresate, bensulfuron (-methyl), bensulide, bentazone, benthiocarb (thiobencarb), benzofenap, bifenox, bromobutide, bromoxynil, butachlor, butamifos, butenachlor, cafenstrole (CH-900), chlomethoxyfen (X-52), chlormethoxynil, chlornitrofen, cinmethylin, CL-303569, CL-303578, cinosulfuron, clomeprop, cumyluron, cyclosulfamuron (AC-322140), cyhalofop(-butyl) (DEH-112), 2,4-D, dichlorprop, dimepiperate, dimethametryn, dithiopyr, DPX47, diuron, dymron (daimuron, dimuron), esprocarb, etobenzanid, fenoxaprop A, fenoxaprop-P-ethyl, fluazifop-butyl, flurenol-n-butyl, GS-32911, haloxyfop, haloxyfop M, hexazinone, HOE-404, HOE-30374, HOK-7501 (HOK-1566), HW-52, imazosulfuron, JC-940, KUH-911 (KIH-2023), KUH-920, KNW-242, KPP-314, MCPA, MCPB, mefenacet, metsulfuron M, molinate, NC-310, NC-311, naproanilide, nitrofen, NSK-850, oxadiargyl (RP-020630, MY-100), oxadiazon, oxyfluorfen, piperophos, pretilachlor, prometryne, propanil, pyrazolate, pyrazosulfuron (-ethyl), pyrazoxyfen, pyributicarb, quinclorac, quizalofop A, sethoxydim, simetryne and trifluralin,
(active compounds of group 2).

Of very particular interest are herbicidal compositions according to the invention characterized by an active content of a heteroaryloxy-acetamide of the formula (I), in which
Het represents 1,2,4-thiadiazolyl or 1,3,4-thiadiazolyl, each of which is substituted by chlorine, dichloromethyl, difluoromethyl, trichloromethyl, trifluoromethyl, chlorodifluoromethyl, fluorodichloromethyl or pentafluoroethyl, and
Ar represents optionally fluorine-, chlorine-, methyl- or trifluoromethyl-substituted phenyl.

Of very particular interest are furthermore synergistic herbicidal compositions according to the invention characterized by an active content of an active compound combination comprising (a) a heteroaryloxy-acetamide of the formula (I), in which
Het represents 1,2,4-thiadiazolyl or 1,3,4-thiadiazolyl, each of which is substituted by chlorine, dichloromethyl, difluoromethyl, trichloromethyl, trifluoromethyl, chlorodifluoromethyl, fluorodichloromethyl or pentafluoroethyl, and
Ar represents optionally fluorine-, chlorine-, methyl- or trifluoromethyl-substituted phenyl.
(active compound of group 1), and (b) one or two compounds from the following group of herbicidally active compounds for use in rice crops ("rice herbicides", named by common names or code numbers):
AKD-741, amiprophos(-methyl), anilofos, benfuresate, bensulfuron(-methyl), bensulide, bentazone, benthiocarb (thiobencarb), benzofenap, bifenox, bromobutide, bromoxynil, butachlor, butamifos, butenachlor, cafenstrole (CH-900), chlomethoxyfen (X-52), chlormethoxynil, chlornitrofen, cinmethylin, CL-303569, CL-303578, cinosulfuron, clomeprop, cumyluron, cyclosulfamuron (AC-322140), cyhalofop(-butyl) (DEH-112), 2,4-D, dichlorprop, dimepiperate, dimethametryn, dithiopyr, DPX-47, diuron, dymron (daimuron, dimuron), esprocarb, etobenzanid, fenoxaprop A, fenoxaprop-P-ethyl, fluazifop-butyl, flurenol-n-butyl, GS-32911, haloxyfop, haloxyfop M, hexazinone, HOE404, HOE-30374, HOK-7501 (HOK-1566), HW-52, imazosulfuron, JC-940, KUH-911 (KIH-2023), KUH-920, KNW-242, KPP-314, MCPA, MCPB, mefenacet, metsulfuron M, molinate, NC-310, NC-311, naproanilide, nitrofen, NSK-850, oxadiargyl (RP-020630, MY-100), oxadiazon, oxyfluorfen, piperophos, pretilachlor, prometryne, propanil, pyrazolate, pyrazosulfuron (-ethyl), pyrazoxyfen, pyributicarb, quinclorac, quizalofop A, sethoxydim, simetryne and trifluralin,
(active compounds of group 2).

Examples of the compounds of the formula (I) to be used as co-components according to the invention are:
N-i-propyl-N-phenyl-α-(5-trifluoromethyl-1,3,4-thiadiazol-2-yl-oxy)-acetamide, N-i-propyl-N-(2-chloro-phenyl)-α-(5-trifluoromethyl-1,3,4-thiadiazol-2-yl-oxy)-acetamide, N-i-propyl-N-(3-chloro-phenyl)-α-(5-trifluoromethyl-1,3,4-thiadiazol-2-yl-oxy)-acetamide, N-i-propyl-N-(4-chloro-phenyl)-α-(5-trifluoromethyl-1,3,4-thiadiazol-2-yl-oxy)-acetamide, N-i-propyl-N-(2-fluoro-phenyl)-α-(5-trifluoromethyl-1,3,4-thiadiazol-2-yl-oxy)-acetamide, N-i-propyl-N-(3-fluoro-phenyl)-α-(5-trifluoromethyl-1,3,4-thiadiazol-2-yl-oxy)-acetamide, N-i-propyl-N-(4-fluoro-phenyl)-α-(5-trifluoromethyl-1,3,4-thiadiazol-2-yl-oxy)-acetamide, N-i-propyl-N-(2,4-difluoro-phenyl)-α-(5-trifluoromethyl-1,3,4-thiadiazol-2-yl-oxy)-acetamide, N-i-propyl-N-(3,4-difluoro-phenyl)-α-(5-trifluoromethyl-1,3,4-thiadiazol-2-yl-oxy)-acetamide, N-i-propyl-N-(2-methyl-phenyl)-α-(5-trifluoromethyl-1,3,4-thiadiazol-2-yl-oxy)-acetamide, N-i-propyl-N-(3-methyl-phenyl)-α-(5-trifluoromethyl-1,3,4-thiadiazol-2-yl-oxy)-acetamide, N-i-propyl-N-(4-methyl-phenyl)-α-(5-trifluoromethyl-1,3,4-thiadiazol-2-yl-oxy)-acetamide, N-i-propyl-N-(3-trifluoromethyl-phenyl)-α-(5-trifluoromethyl-1,3,4-thiadiazol-2-yl-oxy)-acetamide and N-i-propyl-N-(4-trifluoromethyl-phenyl)-α-(5-trifluoromethyl-1,3,4-thiadiazol-2-yl-oxy)-acetamide.

The compound N-i-propyl-N-(4-fluoro-phenyl)-α-(5-trifluoromethyl-1,3,4-thiadiazol-2-yl-oxy)-acetamide—referred to as compound (I-1)—may be emphasized in particular as active compound of the formula (I).

The compounds of the formula (I) are described in the abovementioned patent applications and patent documents.

Surprisingly, it has now been found that the heteroaryloxy-acetamides of the formula (I) are very suitable for the selective control of weeds in rice crops—in sown as well as in planted rice—and that, additionally, active compound combinations of heteroaryloxy-acetamides of the formula (I) and the abovementioned "rice herbicides" have a particularly high synergistic herbicidal activity while being well tolerated by rice.

Surprisingly, the herbicidal activity of the active compound combinations according to the invention is considerably higher than the sum of the actions of the individual active compounds.

There is therefore an unforeseeable synergistic effect, and not just a supplementary action. The novel active compound combinations are well tolerated by rice crops, also allowing good control of weeds which are otherwise difficult to control.

The novel active compound combinations therefore represent a useful addition to the selective herbicides for use in rice crops.

Weeds which can be well controlled by the active compounds or active compound combinations according to the invention are, for example:

Dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Solanum, Cirsium, Carduus, Sonchus, Rorippa, Rotala, Lindernia, Lamium, Veronica, Abutilon, Emex, Sida, Datura, Viola, Galeopsis, Papaver, Centaurea, Trifolium, Ranunculus, Taraxacum.

Monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

However, the use of the active compound combinations according to the invention is in no way restricted to these genera, but also extends in the same manner to other plants.

The active compound combinations according to the invention exhibit, as already mentioned, an outstanding activity against broad-leaved weeds and grass weeds while being well tolerated by rice crops. Their use as selective herbicides in rice crops is therefore particularly emphasized.

The synergistic effect of the active compound combinations according to the invention is particularly highly pronounced at certain concentration ratios. However, the weight ratios of the active compounds in the active compound combinations can be varied within relatively broad ranges. In general, there are 0.001 to 1000 parts by weight, preferably 0.01 to 100 parts by weight, particularly preferably 0.1 to 10 parts by weight of the compounds referred to above as "rice herbicides" (i.e. the active compounds of group 2) per part by weight of active compound of the formula (I) (i.e. of group 1).

The active compounds or active compound combinations can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulfoxide, and water.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolyzates; suitable dispersants are: for example lignin-sulfite waste liquors and methylcellulose.

Adhesives such as carboxymethylcellulose and natural and synthetic polymers in the form of powders, granules or latices such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound or active compound combination, preferably between 0.5 and 90%.

In general, the active compounds or active compound combinations according to the invention are applied in the form of ready mixes. However, the active compounds in the active compound combinations can also be formulated individually and mixed upon application, that is to say applied in the form of tank mixes.

The new active compound combinations as such or in the form of their formulations can also be used as mixtures with further known rice herbicides for controlling weeds, finished formulations or tank mixes again being possible. Mixtures with other known active compounds such as fungicides, insecticides, acaricides, nematicides, bird repellants, growth promoters, plant nutrients and soil conditioners, are also possible. Furthermore, it may be advantageous for specific purposes, in particular when using the post-emergence method, to incorporate mineral or vegetable oils (for example "Oleo Dupont 11E", which is commercially available) or ammonium salts such as, for example, ammonium sulfate or ammonium thiocyanate which are tolerated by plants, as further additives in the formulations.

The active compound combinations according to the invention can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or spreading.

The active compound combinations according to the invention can be applied either before or after emergence of the plants. They can also be incorporated into the soil before sowing.

The rates of application of the active compounds or active compound combinations according to the invention can be varied within a substantial range. They depend essentially on the nature of the desired effect. In general, the rates of application are between 10 g and 10 kg of active compound or active compound combination per hectare of soil surface, preferably between 50 g and 5 kg per ha, in particular between 100 g and 2 kg per ha.

While the individual active compounds show weaknesses in their herbicidal activity, the combinations according to the invention all show very efficient and broadly effective control of the weeds which are mainly found in rice, and this control exceeds a simple sum of the activities.

In herbicides, a synergistic effect is always present when the herbicidal activity of the active compound combination exceeds that of the active compounds applied individually.

The expected activity for a given combination of two herbicides can be calculated as follows (cf. Colby, S. R.; "Calculating synergistic and antagonistic responses of herbicide combinations", Weeds 15, pages 20–22, 1967):

If $X$=% damage by herbicide A (active compound of group 1) at the rate of application of p kg/ha and $Y$=% damage by herbicide B (active compound of group 2) at the rate of application of q kg/ha and $E$=the expected damage caused by herbicides A and B at a rate of application of p and q kg/ha, then $E = X + Y - (X*Y/100)$.

If the actual damage exceeds the calculated value, the combination is super-additive with regard to its activity, i.e. it shows a synergistic effect.

Use experiments with the active compound combinations according to the invention reveal that the herbicidal activity of the active compound combinations according to the invention exceeds the calculated value, i.e. that the new active compound combinations have a synergistic action.

USE EXAMPLES

Example A/greenhouse

Test on planted paddy rice/water surface treatment

Solvent: 5 parts by weight of acetone

Emulsifier: 1 part by weight of benzyloxy polyglycol ether

To prepare a suitable active compound preparation, one part by weight of active compound is mixed with the stated amount of solvent, the stated amount of emulsifier is added and the concentrate is diluted to the desired concentration.

Containers for plants (dimensions 20 cm×20 cm×9 cm; surface 1/2000 Ar) are filled with soil from a rice field. Two rice plants (variety: Kinmaze) in the 2–3-leaf stage (height: about 10–15 cm) are planted in each of the containers: seeds of *Echinochloa crus galli*, *Scirpus juncoides* and *Monochoria vaginalis* and small rhizome cuttings of *Eleocharis acicularis L.* are sown into the soil, which is kept moist. Five days after planting the rice, the soil is flooded to a water-depth of 3 cm; the active compound preparation is applied to the water surface. The active compound concentration in the preparation is not important, only the application rate of the active compound per surface unit is decisive.

After the application of the active compound, a vertically descending stream of water through the plant containers of a velocity of 2–3 cm per day is maintained for two days. Thereafter, the experiments are kept under conditions of flooding at a water depth of 3 cm.

3 weeks after the active compound application, the degree of damage to the plants is rated in % damage (or action of weed) in comparison with an untreated control.

Definitions:

0%=no action/damage (as untreated control) 100%=total destruction

Active compounds, application rates and results are shown in each case in the tables A-1 to A-3 below; the abbreviations used in the tables have the following meanings:

(I-1) = N-i-propyl-N-(4-fluoro-phenyl)-α-(5-trifluromethyl-1,3,4-thiadiazol-2-yl-oxy)-acetamide;

(A)=Bensulfuron-methyl (=methyl 2-[[[[(4,6dimethoxy-2-pyrimidinyl)- amino]-carbonyl]amino]-sulfonyl]-methyl]benzoate);

(B)=MCPB (=4-(4-chloro-2-methylphenoxy)-butyric acid);

(C)=Benthiocarb (=S-4-chlorobenzyl N,N-diethyl-thiocarbamate);

found=damage or activity (in percent) found;

calc.=damage or activity (in percent) calculated using the Colby formula above.

Results:

As shown by the following test results, the activity of the individual components against their target weeds left little scope for improving the activity in tank mixes. In spite of this, it was possible to demonstrate synergistic activity of all tank mixes against *Echinochloa crus galli*.

The mixtures (I-1)+bensulfuron-methyl (A) and (I-1)+ MCPB (B) also showed synergistic activity against *Eleocharis acicularis* and *Scirpus juncoides*.

The tolerability in paddy rice of all herbicides from the active compound group 2 tested was not adversely affected by joint application with the active compound (I-1), which up to now has not been used in rice cultivation.

TABLE A-1

| Active compound or active compound combination | Application rate g/ha (active compound) | Test plants damage or activity in % | | | | | | | | | |
|---|---|---|---|---|---|---|---|---|---|---|---|
| | | *Echinochloa crus galli* | | *Eleocharis acicularis* | | *Scirpus juncoides* | | *Monochoria vaginalis* | | Paddy rice (Oryza sp.) | |
| | | found | calc. | found | calc. | found | calc. | found | calc. | found | calc. |
| (I-1) - known - | 25 | 90 | | 40 | | 60 | | 40 | | 10 | |
| (A) - known - | 60 | 60 | | 90 | | 90 | | 100 | | 10 | |
| (I-1) + (A) - according to the invention - | 25 + 60 | 100 | 96 | 100 | 94 | 100 | 96 | 100 | 100 | 0 | 20 |

TABLE A-2

| Active compound or active compound combination | Application rate g/ha (active compound) | Test plants damage or activity in % | | | | | | | | |
|---|---|---|---|---|---|---|---|---|---|---|
| | | Echinochloa crus galli | | Eleocharis acicularis | | Scirpus juncoides | | Monochoria vaginalis | | Paddy rice (Oryza sp.) | |
| | | found | calc. | found | calc. | found | calc. | found | calc. | found | calc. |
| (I-1) - known - | 25 | 90 | | 40 | | 60 | | 40 | | 10 | |
| (B) - known - | 250 | 50 | | 90 | | 90 | | 90 | | 0 | |
| (I-1) + (B) - according to the invention - | 25 + 250 | 100 | 95 | 100 | 94 | 100 | 96 | 95 | 94 | 5 | 10 |

TABLE A-3

| Active compound or active compound combination | Application rate g/ha (active compound) | Test plants damage or activity in % | | | |
|---|---|---|---|---|---|
| | | Echinochloa crus galli | | Paddy rice (Oryza sp.) | |
| | | found | calc. | found | calc. |
| (I-1) - known - | 25 | 90 | | 10 | |
| (C) - known - | 250 | 70 | | 0 | |
| (I-1) + (C) - according to the invention - | 25 + 250 | 100 | 97 | 10 | 10 |

We claim:

1. A method for the selective control of unwanted vegetation in rice crops, comprising applying an herbicidally effective amount of a compound N-i-propyl-N-(4-fluoro-phenyl)-α-(5-trifluoromethyl-1,3,4-thiadiazol-2-yl-oxy)-acetamide alone or in combination with a compound selected from the group consisting of methyl 2-[[[[[(4,6-dimethoxy-2-pyrimidinyl)-amino]-carbonyl]amino]-sulfonyl]-methyl]benzoate, 4-(4-chloro-2-methylphenoxy)-butyric acid, and S-4-chlorobenzyl N,N-diethyl-thiocarbamate to such unwanted vegetation or to a locus from which it is desired to exclude unwanted vegetation, wherein the rate of application of the compound alone or the compound in combination is between about 50 g and 5 kg per ha.

2. A method for the selective control of unwanted vegetation in rice crops, comprising applying an herbicidally effective amount of a compound N-i-propyl-N-(4-fluoro-phenyl)-α-(5-trifluoromethyl-1,3,4-thiadiazol-2-yl-oxy)-acetamide to such unwanted vegetation or to a locus from which it is desired to exclude unwanted vegetation.

3. A synergistic herbicidal composition for use in rice cultivation comprising an herbicidally effective amount of a combination which comprises N-i-propyl-N-(4-fluoro-phenyl)-α-(5-trifluoromethyl-1,3,4-thiadiazol-2-yl-oxy)-acetamide and a compound selected from the group consisting of methyl 2-[[[[[(4,6-dimethoxy-2-pyrimidinyl)-amino]-carbonyl]amino]-sulfonyl]-methyl]benzoate, 4-(4-chloro-2-methylphenoxy)-butyric acid, and S-4-chlorobenzyl N,N-diethyl-thiocarbamate and an extender, wherein the weight ratio of N-i-propyl-N-(4-fluoro-phenyl)-α-(5-trifluoromethyl-1,3,4-thiadiazol-2-yl-oxy)-acetamide to methyl 2-[[[[[(4,6-dimethoxy-2-pyrimidinyl)-amino]-carbonyl]amino]-sulfonyl]-methyl]benzoate, 4-(4-chloro-2-methylphenoxy)-butyric acid, and S-4-chlorobenzyl N,N-diethyl-thiocarbamate is between about 1:0.01 and 1:100.

4. The composition according to claim 3 wherein said combination comprises N-i-propyl-N-(4-fluoro-phenyl)-α-(5-trifluoromethyl-1,3,4-thiadiazol-2-yl-oxy)-acetamide and methyl 2-[[[[[(4,6-dimethoxy-2-pyrimidinyl)-amino]-carbonyl]amino]-sulfonyl]-methyl]benzoate.

5. The composition according to claim 3 wherein said combination comprises N-i-propyl-N-(4-fluoro-phenyl)-α-(5-trifluoromethyl-1,3,4-thiadiazol-2-yl-oxy)-acetamide and 4-(4-chloro-2-methylphenoxy)-butyric acid.

6. The composition according to claim 3 wherein said combination comprises N-i-propyl-N-(4-fluoro-phenyl)-α-(5-trifluoromethyl-1,3,4-thiadiazol-2-yl-oxy)-acetamide and S-4-chlorobenzyl N,N-diethyl-thiocarbamate.

7. The composition according to claim 3 wherein the weight ratio of N-i-propyl-N-(4-fluoro-phenyl)-α-(5-trifluoromethyl-1,3,4-thiadiazol- 2-yl-oxy)-acetamide to methyl 2-[[[[[(4,6-dimethoxy-2-pyrimidinyl)-amino]-carbonyl]amino]-sulfonyl]-methyl]benzoate, 4-(4-chloro-2-methylphenoxy)-butyric acid, and S-4-chlorobenzyl N,N-diethyl-thiocarbamate is between about 1:0.1 and 1:10.

8. A method for the selective control of unwanted vegetation in rice crops, wherein the composition according to claim 3 is allowed to act upon the rice crops.

* * * * *